(12) United States Patent
Zacharopoulos et al.

(10) Patent No.: US 8,353,112 B2
(45) Date of Patent: Jan. 15, 2013

(54) SIGNAL EMITTING OR RECEIVING POINTER

(76) Inventors: Nicholas G. Zacharopoulos, New City, NY (US); Robert Boyd, Long Island City, NY (US)

(*) Notice: Subject to any disclaimer, the term of this patent is extended or adjusted under 35 U.S.C. 154(b) by 390 days.

(21) Appl. No.: 12/819,899

(22) Filed: Jun. 21, 2010

(65) Prior Publication Data

US 2010/0324860 A1    Dec. 23, 2010

Related U.S. Application Data

(60) Provisional application No. 61/218,617, filed on Jun. 19, 2009.

(51) Int. Cl.
*G01C 15/02* (2006.01)

(52) U.S. Cl. ........................................ 33/227; 33/1 CC

(58) Field of Classification Search .................. 33/1 CC, 33/227, 512, DIG. 21
See application file for complete search history.

(56) References Cited

U.S. PATENT DOCUMENTS

| | | | | | |
|---|---|---|---|---|---|
| 5,784,792 | A | * | 7/1998 | Smith | 33/227 |
| 5,823,679 | A | * | 10/1998 | Hollander et al. | 33/DIG. 21 |
| 6,028,665 | A | * | 2/2000 | McQueen | 33/227 |
| 7,296,360 | B2 | * | 11/2007 | El-Katcha et al. | 33/DIG. 21 |
| 7,690,124 | B1 | * | 4/2010 | Henry | 33/286 |
| 2010/0080087 | A1 | * | 4/2010 | Shupp | 33/355 R |
| 2011/0216199 | A1 | * | 9/2011 | Trevino et al. | 33/264 |

* cited by examiner

*Primary Examiner* — G. Bradley Bennett
(74) *Attorney, Agent, or Firm* — Collen IP; Donald J. Ranft

(57) ABSTRACT

A signal emitting or receiving pointer and method for its use to enable the determination of the geometrical center of a rotating gantry. The pointer has emitters or receivers installed on the pointer and the signals sent or received as the gantry is rotated allow the calculation of the geometrical center of a rotating gantry.

13 Claims, 12 Drawing Sheets

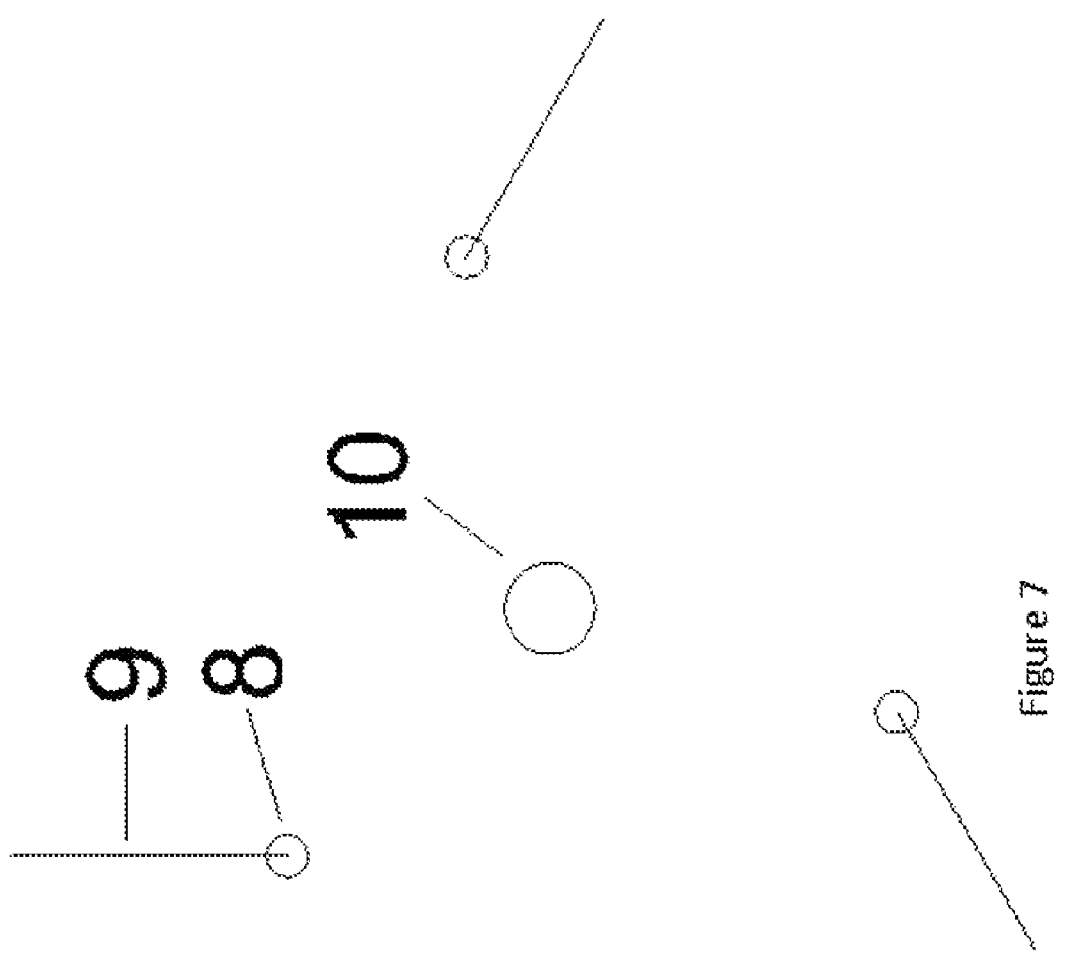

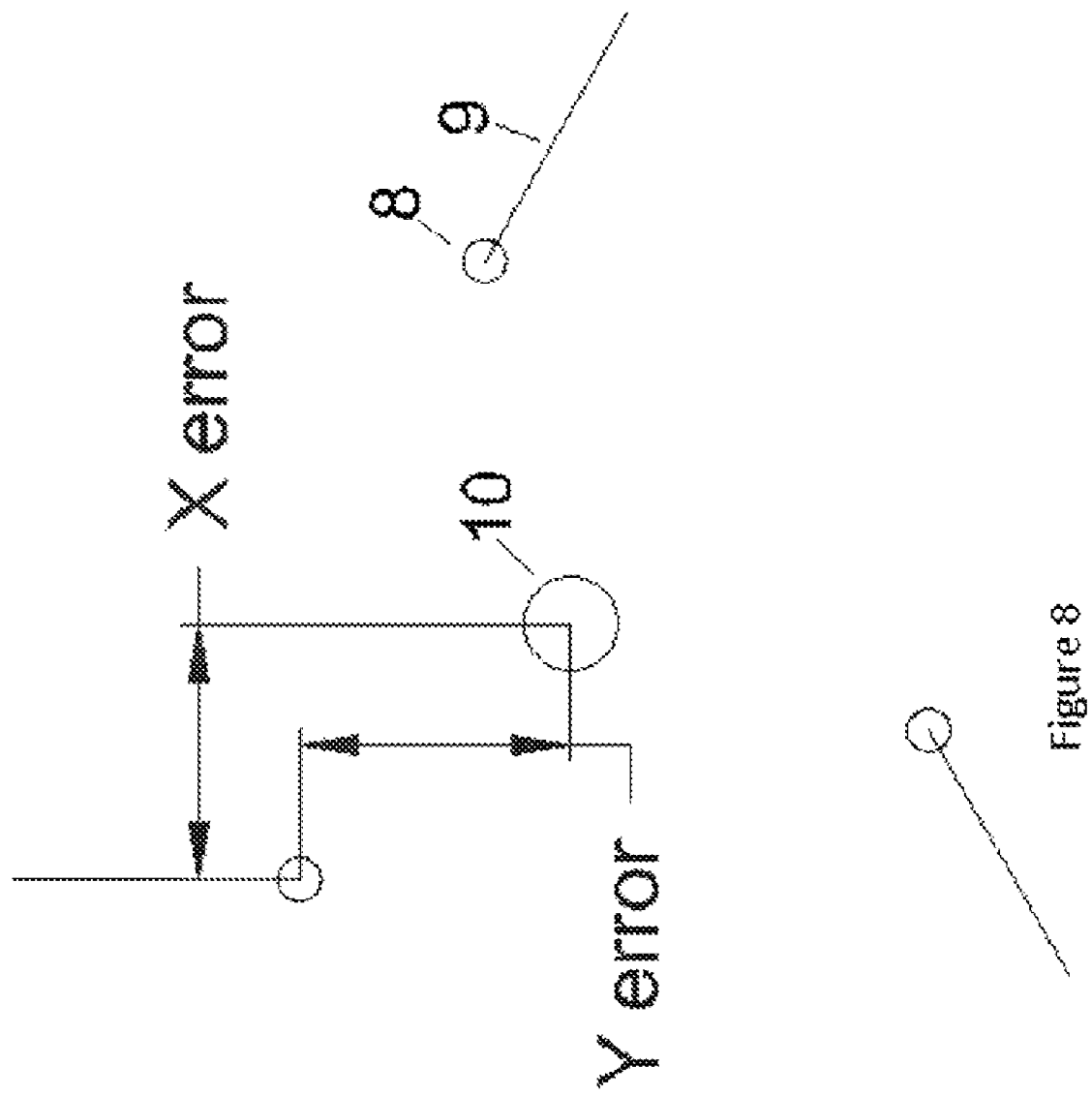

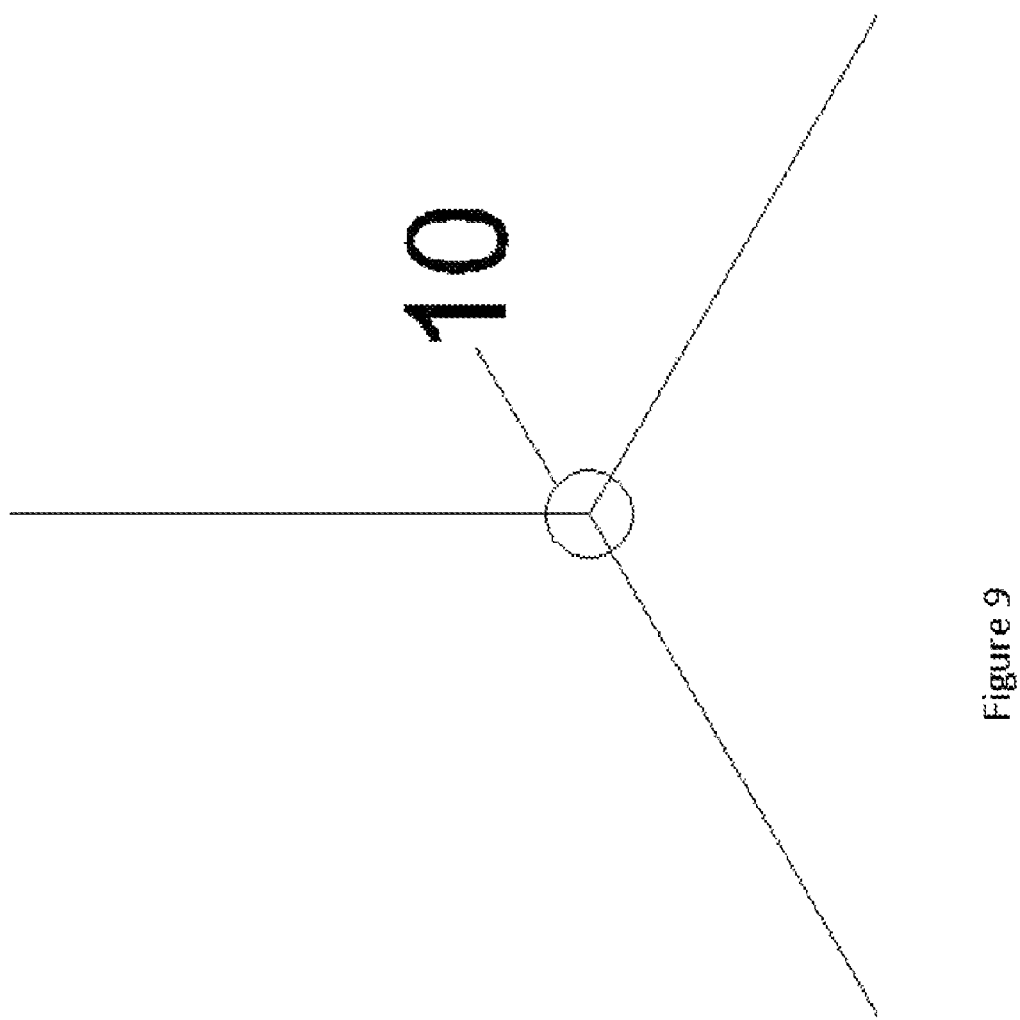

SIGNAL EMITTING OR RECEIVING POINTER

BACKGROUND

In Radiation Oncology, a linear accelerator is used to deliver radiation beams to the patient from a rotating gantry.

One of the critical elements of the accuracy of the treatment is the geometrical accuracy of the gantry rotation. The point in space that defines the center of rotation must be determined before putting the system into use and must be verified routinely as part of a quality assurance program.

In order to determine the point in space that corresponds to the rotational axis, mechanical front pointers have been routinely used (see FIG. 1).

The Mechanical Front Pointer attaches to the treatment head and physically points to a location in space with a very accurate tip (approximately 1 mm). With the Front Pointer attached, the gantry can be rotated through a full 360° rotation while observing the tip of the Mechanical Front Pointer. The position of the Mechanical Front Pointer tip can then be adjusted to minimize the path of travel of the tip. Once this is done the Front Pointer tip is positioned at the center of rotational gantry.

One main problem with Mechanical Front Pointers is that they require the user to document (usually with a piece of paper that is placed adjacent to the tip of the Front Pointer) the tip path, and then iteratively make adjustments until the tip path is as tight as possible. Doing so introduces many errors due to parallax between the paper and the Front Pointer tip and human error in placing a dot with a pen onto the paper. Not only is this process subject to human error, but it is very time consuming.

BRIEF DESCRIPTION OF THE DRAWINGS

FIG. 7 is the graphical results of the software analysis of the configuration shown in FIG. 6.

FIG. 8 is example of determination of the beam emitting front pointer adjustment.

FIG. 9 is the results of analysis after the beam emitting front pointer is properly adjusted.

DETAILED DESCRIPTION OF PREFERRED EMBODIMENTS

Figure 1:
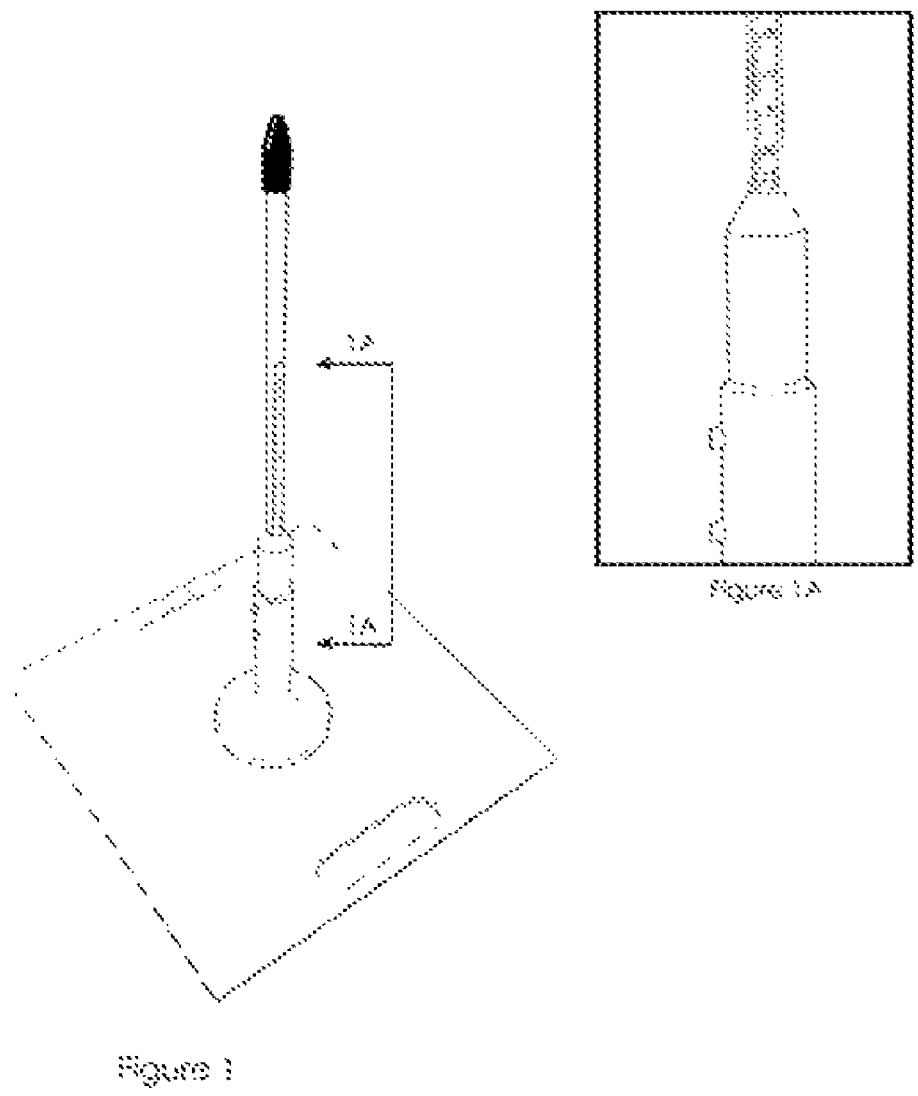
FIG. 1 depicts a mechanical front pointer.
Figure 2:
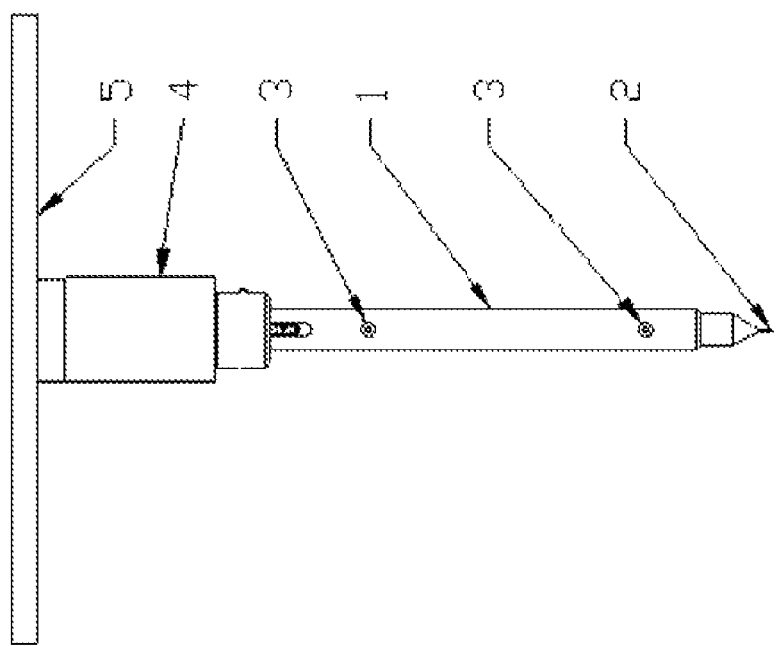
FIG. 2 depicts a beam emitting pointer.
Figure 3:
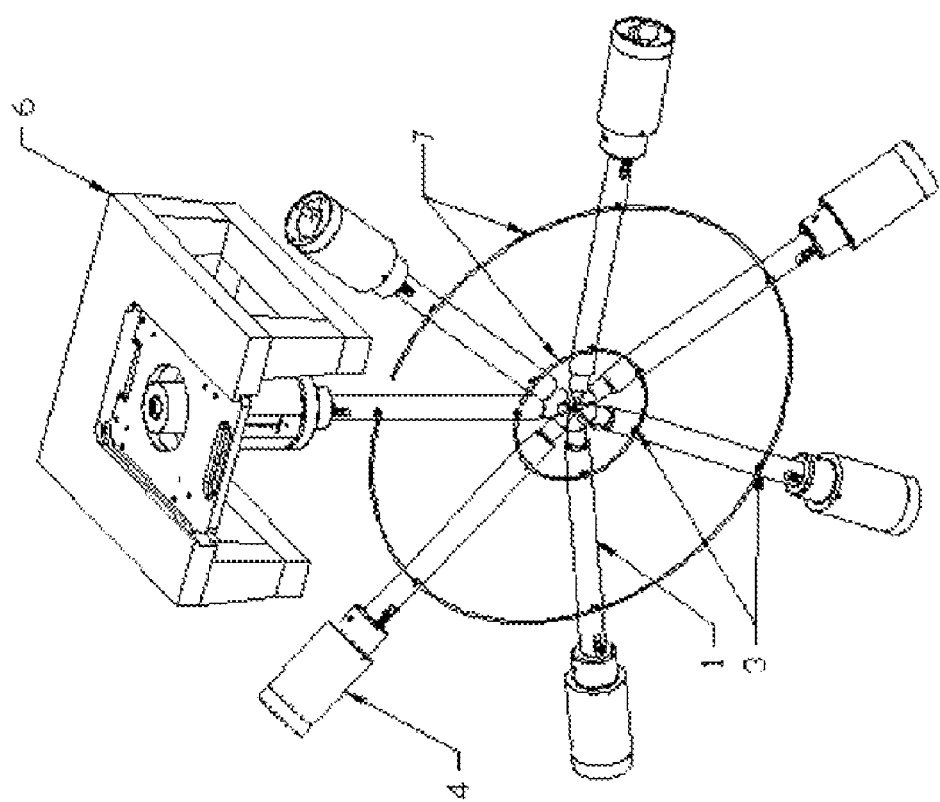
FIG. 3 depicts the concentric paths created by the 360° rotation of a light beam emitting pointer.

Instead of the typical mechanical pointer, a front pointer with a minimum of 2 signal emitters (e.g. light emitting diodes; radio frequency transmitters, optical reflectors) is attached to the head on the gantry. Any type of emitter can be used as long as a means to locate and record the position of the emitter (as the gantry rotates) within a fixed coordinate system is available. The pointer (1) shown in FIG. 2 has 2 light emitters (3) such as LED's. The distances between the light emitters and to the pointer tip (2) are controlled to an accuracy of 0.005 inches.

The pointer tip (2) is on one end of the pointer with pointer base on its other end. The pointer base in installed on a mounting tray (5) which is designed to slide into a slot on the collimator assembly of the gantry. A scale is included on the pointer so that the distance from the collimator to the tip of the pointer to be determined. A means to secure the pointer when it is set at the desired distance is provided.

Figure 4:
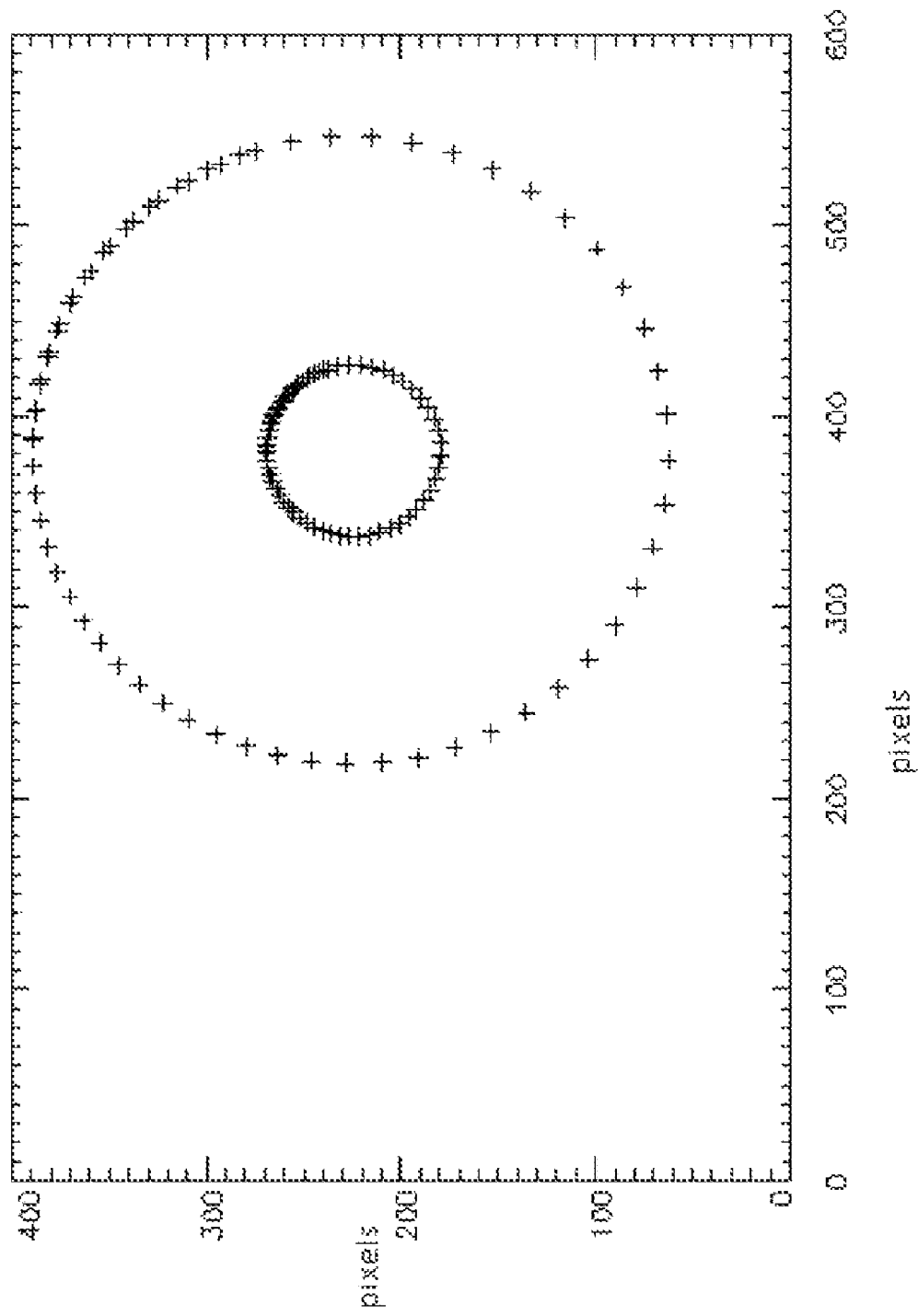
FIG. 4 is software analysis results showing light source centers from all frames of video.

With the front pointer attached to the collimator, a 360° rotation of the gantry will create light paths of concentric circles that can be captured by a receiver. In this case, since LEDs are being used, the receiver could be a standard video camera securely mounted focused towards the rotating gantry). The video can be exported to still images and each frame can be analyzed (typically with software) to determine the center position of all LEDs (FIG. 4). Each still image can be calibrated geometrically (e.g. image pixels per cm) based on the known distance between the light sources. Since the signal receiver is stationary throughout the data collection process, a coordinate system is inherently created by the receiver that can be used to trace the position of the real front pointer tip. Software analysis can then also be used to draw a vector along each light pair towards the center of rotation (see FIG. 5) within this coordinate system.

A final analysis plot created provides the path of the calculated pointer tip (2) as the gantry was rotated. It enables the gantry center of rotation and the radius of the path traveled to be determined quickly and accurately while eliminating human error.

Figure 5:
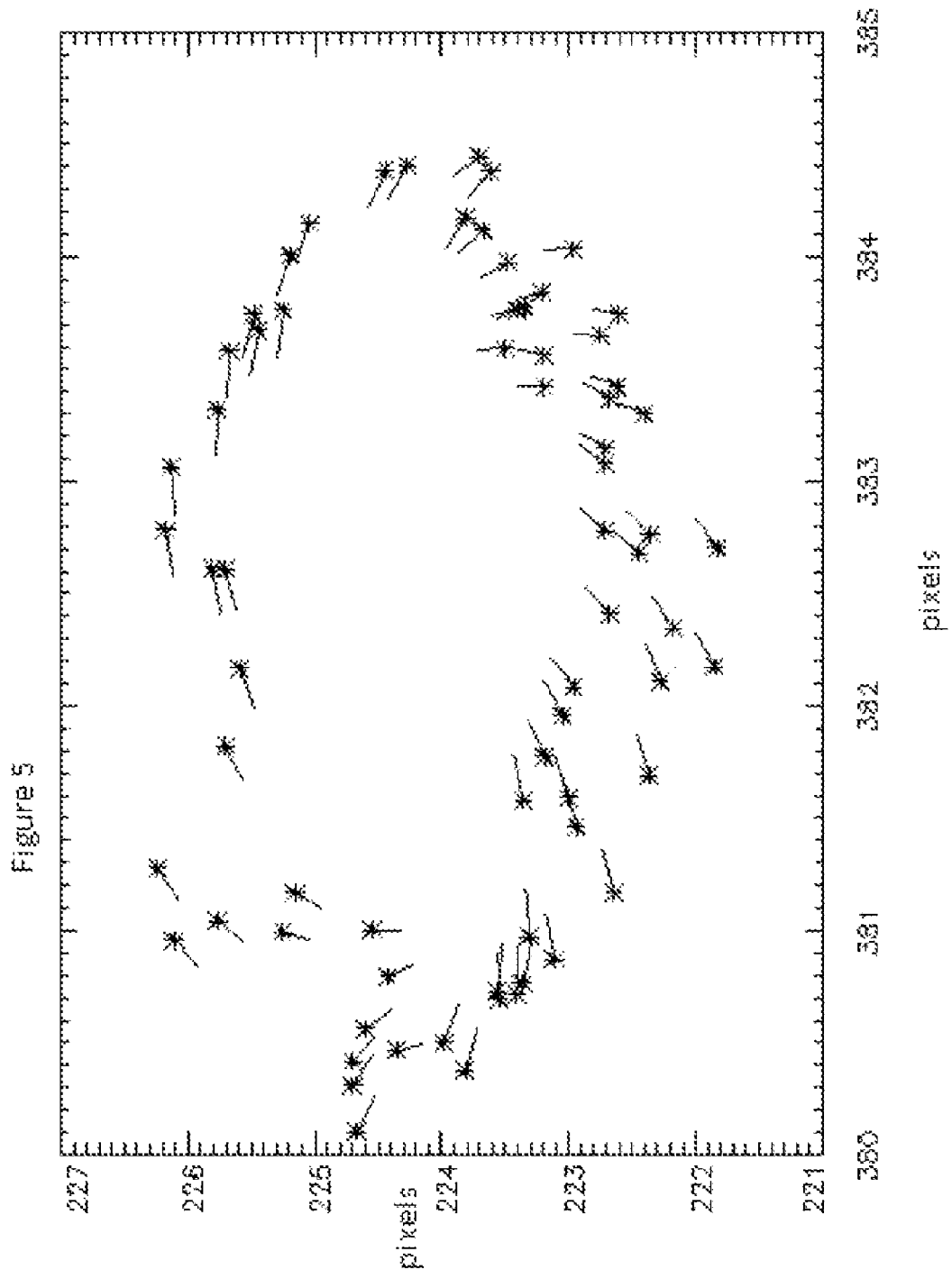
FIG. 5 is the final results of the beam emitting pointer Software Analysis.
Figure 6:
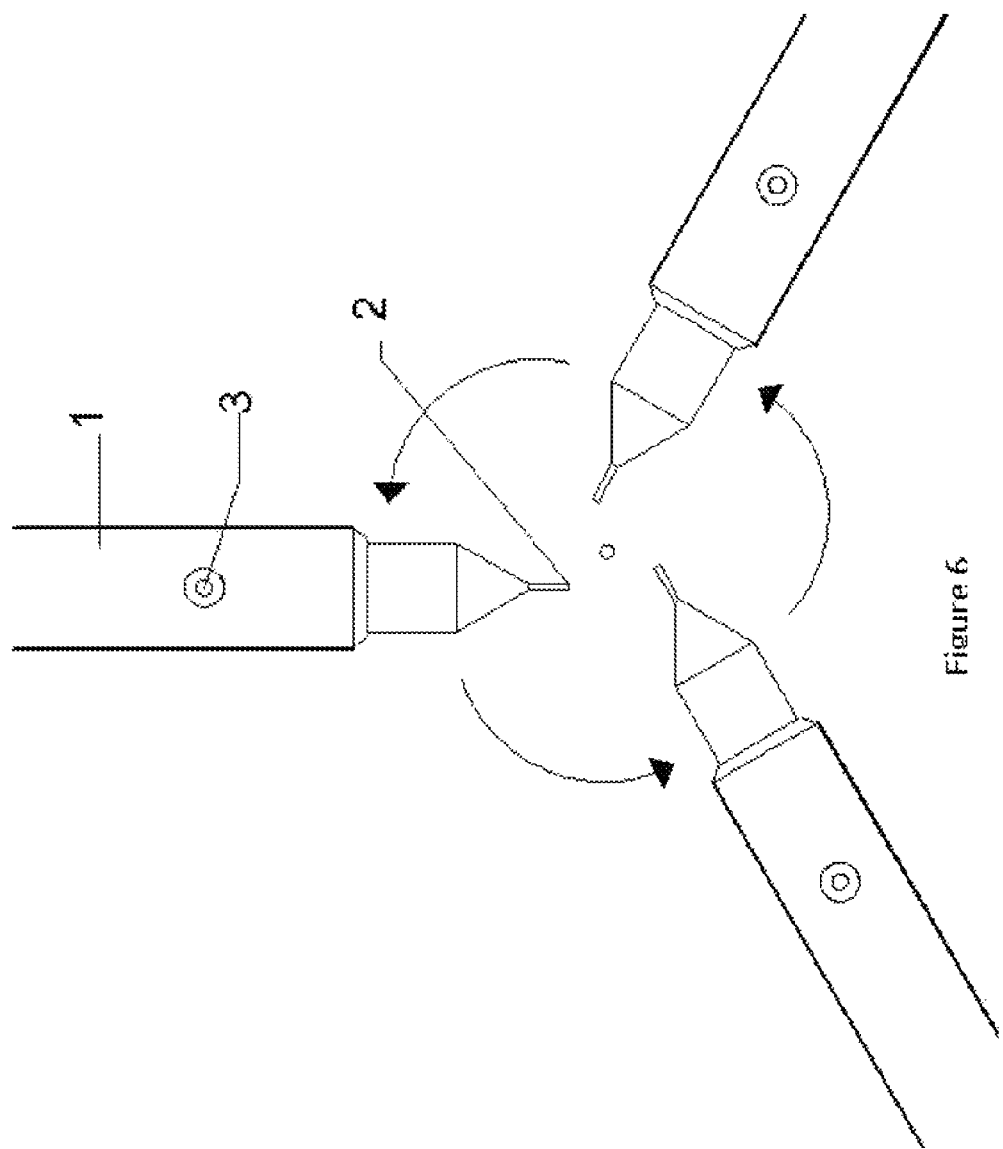
FIG. 6 is the rotation of beam emitting pointer about iso-center (arrow shows the direction of rotation).

In order to understand and interpret the result shown in FIG. 5, a simple illustration of three movie frames of a rotating front pointer is shown in FIG. 6. In this example, it is clear that the front pointer tip (2) is not perfectly positioned at the center of rotation (at this point, keep in mind the center of rotation is not yet known, but is shown in the graphic for the purpose of illustration).

A graphical representation of the results of images captured for the positions shown in FIG. 6 is shown in FIG. 7. The position of the front pointer tip is calculated based on the measured positions of the emitters within the coordinate system of the receiver, the known distance between the emitters, the known distance between the emitters and the pointer tip.

A point (8) is then drawn representing the calculated location of the front-pointer tip (2) and a vector (9) is drawn representing the pointer direction. The vector is the result of creating a line between the 2 emitters captured on an image and then extending it to the calculated pointer tip.

FIG. 7 can then be used to estimate the amount of adjustment required to position the front-pointer tip so that it is perfectly aligned with the center of rotation. First, the center of rotation can be estimated since it is, by definition, at the center of all the determined tip points. Once the center is estimated, then the real adjustment to the pointer tip (2) position can be determined as shown in FIG. 8. As can be seen in FIG. 8, the adjustments can be determined from any of the data points, as long as errors are calculated in a coordinate system that is aligned with the vector corresponding to the point.

Figure 10B:
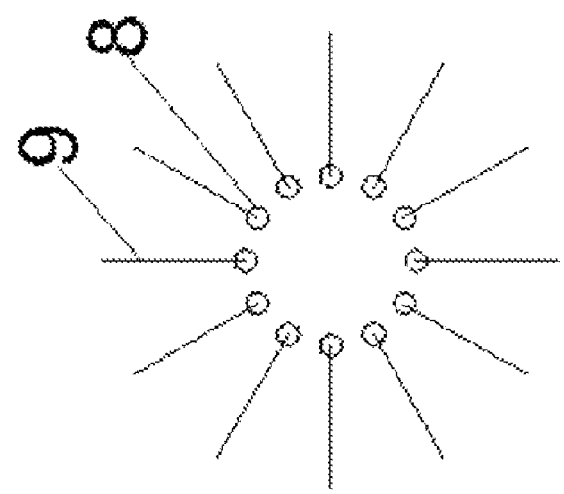
FIG. 10B depicts an example of vectors which would be created as the results of analysis of video images with captured positions of pointer during 360° rotation of gantry (with the pointer position relative to the center gantry rotation as shown in FIG. 10A).
Figure 10A:
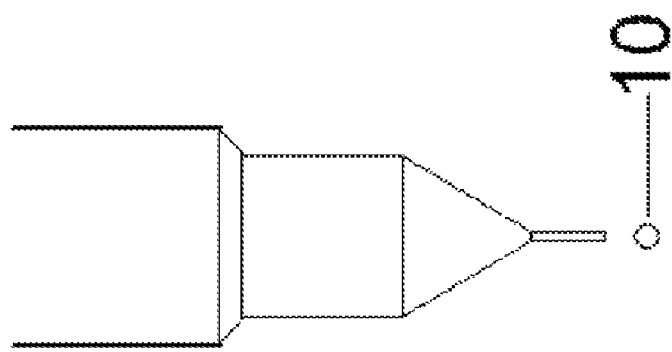
FIG. 10A depicts an example of a center of gantry rotation (10) relative to the pointer.
Figure 11B:
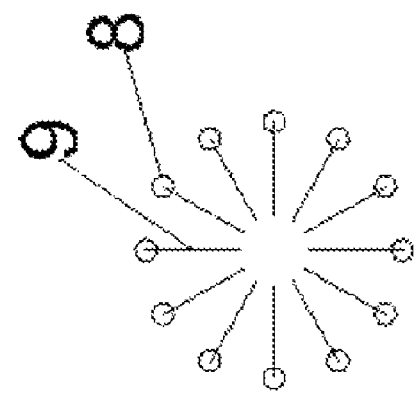
FIG. 11B depicts an example of vectors which would be created as the results of analysis of video images with captured positions of pointer during 360° rotation of gantry (with the pointer position relative to the center gantry rotation as shown in FIG. 11A).
Figure 11A:
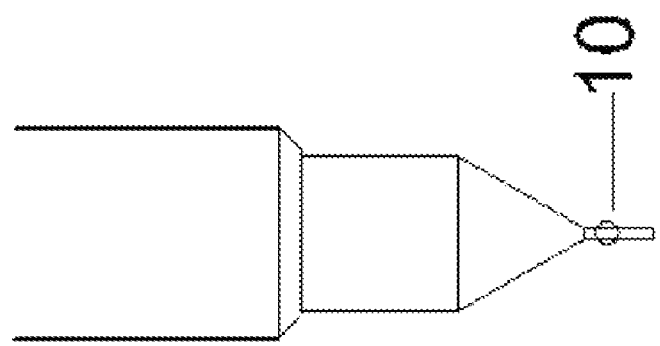
FIG. 11A depicts a second example of a center of gantry rotation (10) relative to the pointer.
Figure 12B:
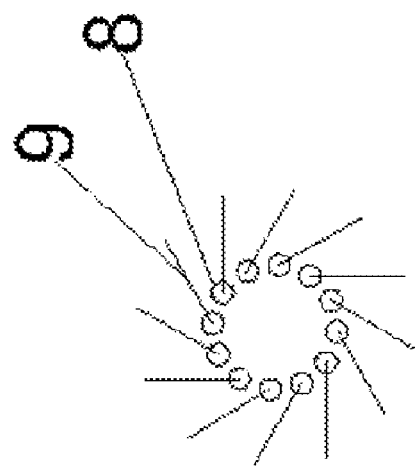
FIG. 12B depicts an example of vectors which would be created as the results of analysis of video images with captured positions of pointer during 360° rotation of gantry (with the pointer position relative to the center gantry rotation as shown in FIG. 12A).
Figure 12A:
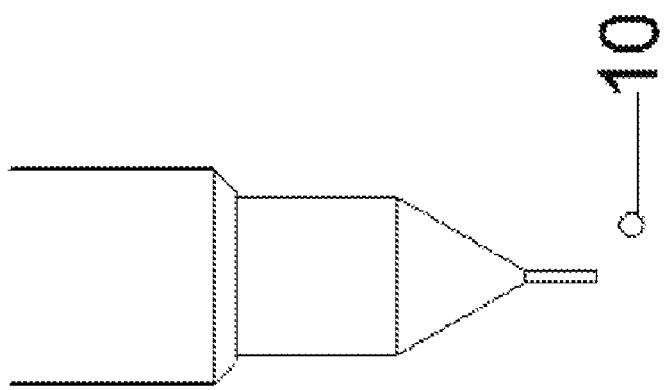
FIG. 12A depicts a third example of a center of gantry rotation (10) relative to the pointer.

Once the front-pointer tip is adjusted, a subsequent data set can be collected and analyzed to ensure that the tip was properly adjusted. Examples of possible gantry misalignment (shown in relation to pointer position captured on video) are depicted on FIGS. 10A, 11A, and 12A. Examples of corresponding vectors (9) which would be created for each of these misalignments as the result of analysis of the images taken during gantry rotation are shown on FIGS. 10B, 11B, and 12B.

An added benefit of this new design is that the process of determining the gantry rotation with the signal emitting front-pointer not only positions the pointer in the correct position, but also creates a record of the accuracy of this position. With previous mechanical front-pointers, positioning of the tip and then recording the accuracy was a two-step process.

In another embodiment of a receiver is mounted on the pointer instead of emitters. As with the emitters the distance between the receiver and the pointer tip (2) is controlled to an accuracy of 0.005 inches. Signal transmitters are mounted at set positions within the room with direct line of sight to the pointer as the gantry is rotated. The position of the receiver on the pointer is then determined by the calculation of the distance from each of the transmitters during rotation.

Having described preferred embodiments which serve to illustrate various concepts, structures and techniques which are the subject of this patent, it will now become apparent to those of ordinary skill in the art that other embodiments incorporating these concepts, structures and techniques may be used. Accordingly, it is submitted that that scope of the patent should not be limited to the described embodiments but rather should be limited only by the spirit and scope of the following claims.

We claim the following:

1. A signal pointer for determining geometric accuracy of a rotating gantry comprising:
    a pointer;
    tip at one end of the pointer;
    an opposite end of the pointer designed for attachment to a collimator assembly; and
    a minimum of two signal emitters installed on the pointer.

2. A signal pointer according to claim 1, in which the signal emitters are light sources.

3. A signal pointer according to claim 1, in which the signal emitters are radio frequency transmitters.

4. A signal pointer according to claim 1, in which the signal emitters are optical reflectors.

5. A signal pointer according to claim 1, further comprising a scale on the pointer to indicate distance from the collimator to the tip of the pointer; and a means to secure the pointer when it is set at the desired distance.

6. A signal pointer for determining geometric accuracy of a rotating gantry comprising:
    a pointer;
    tip at one end of the pointer;
    an opposite end of the pointer designed for attachment to a collimator assembly; and
    a minimum of two signal receivers installed on the pointer.

7. A method for determining the geometric accuracy of a rotating gantry comprising:
    creating a pointer with a minimum of two signal emitters with known distances between each of the emitters and between each emitter and a tip of the pointer;
    installing the pointer on a collimator on the gantry;
    mounting a receiver compatible with the emitter signals at a fixed location capable of monitoring signals from the emitters during rotation of the gantry;
    creating vectors based on the location of the two emitter signals for each position of the gantry as it is rotated;
    calculating the geometric center of the rotating gantry based on an analysis of the vectors;
    adjusting the gantry and collimator, if required to move the pointer tip to the calculated geometric center of the rotating gantry.

8. A method for determining the geometric accuracy of a retaining gantry according to claim 7, wherein the emitters are light sources.

9. A method for determining the geometric accuracy of a retaining gantry according to claim 7, wherein the receiver is a video camera capable of exporting still images.

10. A method for determining the geometric accuracy of a retaining gantry according to claim 8, wherein each still image is calibrated geometrically.

11. A method for determining the geometric accuracy of a retaining gantry according to claim 7, wherein the emitters are radio frequency transmitters.

12. A method for determining the geometric accuracy of a retaining gantry according to claim 7, wherein the emitters are optical reflectors.

13. A method for determining the geometric accuracy of a rotating gantry comprising:
    creating a pointer with a minimum of two signal receivers with known distances between each of the receivers and between each receiver and a tip of the pointer;
    installing the pointer on a collimator on the gantry;
    mounting a minimum of three signal transmitters which are compatible with the receivers at a fixed location capable of transmitting signals to the receivers during rotation of the gantry;
    creating vectors based on the location of the distance to each receiver for each position of the gantry as it is rotated;
    calculating the geometric center of the rotating gantry based on an analysis of the vectors;
    adjusting the gantry and collimator, if required to move the pointer tip to the calculated geometric center of the rotating gantry.

* * * * *